United States Patent
Radley et al.

(10) Patent No.: US 7,104,690 B2
(45) Date of Patent: Sep. 12, 2006

(54) DIAGNOSING SYSTEM FOR AN X-RAY SOURCE ASSEMBLY

(75) Inventors: Ian Radley, Glenmont, NY (US); Michael D. Moore, Alplaus, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 0 days.

(21) Appl. No.: 11/042,602

(22) Filed: Jan. 25, 2005

(65) Prior Publication Data

US 2005/0157849 A1     Jul. 21, 2005

Related U.S. Application Data

(63) Continuation of application No. PCT/US03/23129, filed on Jul. 24, 2003.

(60) Provisional application No. 60/398,966, filed on Jul. 26, 2002.

(51) Int. Cl.
*G01D 18/00*     (2006.01)
(52) U.S. Cl. .................................... 378/207
(58) Field of Classification Search ............... 378/207, 378/117, 118, 119, 121, 210
See application file for complete search history.

(56) References Cited

U.S. PATENT DOCUMENTS

| | | | |
|---|---|---|---|
| 6,212,256 B1 * | 4/2001 | Miesbauer et al. | 378/118 |
| 6,351,517 B1 | 2/2002 | Guru et al. | 378/91 |
| 6,426,997 B1 | 7/2002 | Fuchs et al. | 378/118 |
| 2001/0031036 A1 | 10/2001 | Berezowitz et al. | 378/118 |

FOREIGN PATENT DOCUMENTS

DE     10011294 A1     10/2000

* cited by examiner

*Primary Examiner*—Courtney Thomas
(74) *Attorney, Agent, or Firm*—Jeffrey R. Klembczyk, Esq.; Kevin P. Radigan, Esq.; Heslin Rothenberg Farley & Mesiti, P.C.

(57) ABSTRACT

A diagnostic technique for an x-ray source. A system monitors existing conditions (e.g., tube current Y) in the source to track degradation of certain components to anticipate failure. Storage of past characteristics and reference characteristics is also provided for predicting failure and other operating conditions of the source. Communication techniques are provided for the monitoring and warning functions.

21 Claims, 4 Drawing Sheets

DIAGNOSING SYSTEM FOR AN X-RAY SOURCE ASSEMBLY

CROSS-REFERENCE TO RELATED APPLICATIONS

This application is a continuation of PCT Application PCT/US2003/023129, filed Jul. 24, 2003, and published under the PCT Articles in English as WO 2004/012014 A2 on Feb. 5, 2004. PCT/US2003/023129 claimed priority to U.S. Provisional Application No. 60/398,966, filed Jul. 26, 2002. The entire disclosures of PCT/US2003/023129 and U.S. Ser. No. 60/398,966 are incorporated herein by reference in their entirety. In addition, this application contains subject matter related to the subject matter of the following applications, which are assigned to the same assignee as this application. The below-listed applications are also hereby incorporated herein by reference in their entirety:

"X-RAY TUBE AND METHOD AND APPARATUS FOR ANALYZING FLUID STREAMS USING X-RAYS", by Radley et al., U.S. Ser. No. 60/336,584, filed Dec. 4, 2001;

"A METHOD AND APPARATUS FOR DIRECTING X-RAYS", by Radley, U.S. Ser. No. 60/383,990, filed May 29, 2002;

"X-RAY SOURCE ASSEMBLY HAVING ENHANCED OUTPUT STABILITY", by Radley, U.S. Ser. No. 60/398,965, filed Jul. 26, 2002;

"METHOD AND DEVICE FOR COOLING AND ELECTRICALLY-INSULATING A HIGH-VOLTAGE, HEAT-GENERATING COMPONENT", by Radley, U.S. Ser. No. 60/398,968, filed Jul. 26, 2002; and "AN ELECTRICAL CONNECTOR, A CABLE SLEEVE, AND A METHOD FOR FABRICATING A HIGH-VOLTAGE ELECTRICAL CONNECTION FOR A HIGH VOLTAGE DEVICE", by Radley, U.S. Ser. No. 10/206,531, filed Jul. 26, 2002, and issued on Aug. 24, 2004 as U.S. Pat. No. 6,781,060 B2.

FIELD OF THE INVENTION

The present invention relates generally to an x-ray source, and more particularly, to an x-ray source assembly having a diagnostic system with storage and processing capability to track operating conditions and anticipate failure of the components of the x-ray source assembly.

BACKGROUND OF THE INVENTION

X-ray tubes provide a way of producing x-rays electrically and have seen widespread adaption for x-ray fluorescence spectroscopy, x-ray diffraction crystallographic analyses, and medical and dental applications. Due to the physical nature of the components of an x-ray tube, the operating conditions and properties change over time causing the components to age and eventually fail. When failure occurs (e.g., high voltage discharge or burn out of a filament), the x-ray tube and related instruments and components may be significantly damaged.

Currently, while an x-ray tube is in operation, there is no way to monitor the operating conditions of its components to anticipate failure. Thus, there is no pre-warning of this failure or of the degradation of the components of an x-ray tube.

SUMMARY OF THE INVENTION

The shortcomings of the prior art may be alleviated by using a diagnostic system in accordance with one or more principles of the present invention. The diagnostic system of the present invention may be used in any type of vacuum system such as, for example, an x-ray source or microwave tube. Additionally, other uses may be made of the invention which falls within the scope of the invention but which are not specifically described below.

In one aspect of the invention, there is provided a diagnostic system for an x-ray source. The diagnosing system may include monitoring and processing capabilities to monitor existing operating conditions to track the degradation of certain components of the x-ray source in order to anticipate failure. The diagnosing system may also include storage capabilities for storing past or reference characteristics of the certain components of the x-ray source. More particularly, a diagnosing system in accordance with an aspect of the present invention provides monitoring and processing elements which work to determine characteristics of certain components of the x-ray source.

In accordance with another aspect of the present invention, the diagnosing system may communicate with a network, maintenance personal or another outside source to warn or notify of a potential failure. In accordance with yet another aspect of the present invention, the diagnosing system may direct or control components of an x-ray source assembly based on information collected or contained concerning certain components or operating conditions of such components.

BRIEF DESCRIPTION OF THE DRAWINGS

The foregoing and other objects, features, and advantages of the invention are apparent from the following detailed description taken in conjunction with the accompanying drawings in which.

BEST MODE FOR CARRYING OUT THE INVENTION

Generally, the present invention provides in one aspect an x-ray source having a diagnostic system for monitoring the existing operating conditions of certain components within an x-ray source and for storing data or information concerning the x-ray source and its operation for future evaluation. For example, data related to existing operating conditions collected by the diagnostic system could be compared to past, desired or reference operating conditions to track the operation during the life of an x-ray source component and anticipate failure of that component.

In one aspect, the diagnostic system includes, for example, storage and processing capabilities to store and retrieve information associated with the identity, warranty, or reference operating conditions of the x-ray source assembly and its components. The processing element may be configured to examine and compare existing operating conditions with such stored operating conditions. In monitoring the existing operating conditions, the diagnostic system may employ one or more sensors coupled to certain components of the x-ray source. For example, one sensor might detect the amount of current(s) and voltage passing through a filament of an electron gun in the x-ray source. The processing element of the diagnosing system may also be programmed to convert the detected current and voltage into resistance and to recognize critical resistance values in, for example, the filament.

In another aspect of the present invention, the diagnostic system communicates with the components of the x-ray source and other components outside the x-ray source (e.g., optics, object being x-rayed, power supply). This enables the components of an x-ray source assembly to communicate in order to, for example, optimize and report overall performance, run diagnostics and calibration routines, and report error or failure conditions. In one example, the diagnostic system may communicate with a network or maintenance personnel to warn against failure of a component.

Figure 1:
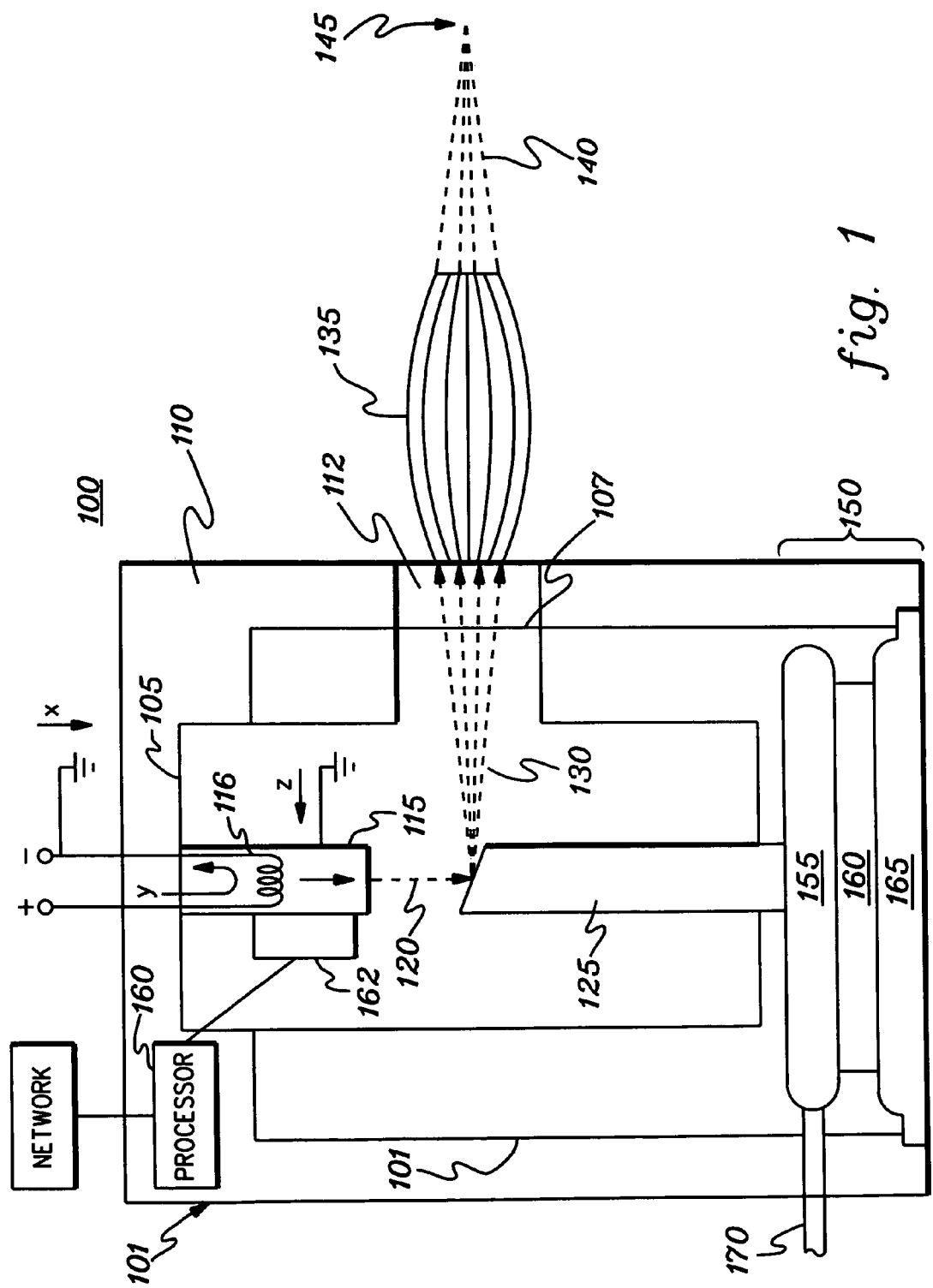
FIG. 1 depicts a cross-sectional view of one embodiment of an x-ray source assembly, in accordance with an aspect of the present invention.

FIG. 1 illustrates in cross-section an elevational view of an x-ray source assembly 100 in accordance with an aspect of the present invention. X-ray source assembly 100 includes a x-ray source 101 comprising a vacuum tight x-ray tube 105 (typically formed of glass or ceramic) having a transmission window 107. X-ray tube 105 houses an electron gun 115 arranged opposite a high-voltage (HV) anode 125. When voltage is applied, electron gun 115 emits electrons from a coil or filament in the form of an electron stream, i.e., an electron beam (e-beam) 120, as is well know in the art. HV anode 125 acts as a target upon which an electron stream may impinge for subsequently producing x-ray radiation, i.e, x-rays 130, also as is well known in the art.

Electron gun 115, in one embodiment, is held at ground potential (zero volts) and conversely HV anode 125 is held at a high voltage potential, typically around 50 kv. As a result, e-beam 120 emitted from electron gun 115 at ground potential is electrically attracted to the surface of HV anode 125, thereby producing x-rays 130 from a source spot on the anode at which e-beam 120 strikes the anode. X-rays 130 are subsequently directed through transmission window 107 of vacuum tight x-ray tube 105. Transmission window 107 is typically formed of a material such as, for example, beryllium (Be) which permits substantially unimpeded transmission of the x-rays while still maintaining the vacuum within x-ray tube 105.

A housing 110 encloses x-ray tube 105. Housing 110 can include an aperture 112 aligned with transmission window 107 and x-ray tube 105. By way of example, aperture 112 could comprise an open aperture in housing 110 or an enclosed aperture defining an air space. Upon transmission through transmission window 107 and aperture 112, x-rays 130 may be collected by an optic 135. In alternate embodiments, the x-rays 130 may illuminate directly on the object, e.g. as used in the medical profession or in baggage scanning, or irradiate food or sterilize materials.

Optic 135 is shown in this example centered about aperture 112 in housing 110. Optic 130 could be affixed to an exterior surface of housing 110, or could be partially disposed within housing 110 to reside within aperture 112 (e.g., to reside against transmission window 107), or could be separately supported from housing 110 but aligned to aperture 112 in housing 110.

In an embodiment employing an optic, Optic 135 could comprise a focusing optic or a collimating optic, by way of example. In FIG. 1, optic 135 is shown to be a focusing element, which is useful when x-ray source 100 is utilized for applications requiring a high intensity, low diameter spot 145. Focusing optic 135 collects x-ray radiation 130 and focuses the radiation into converging x-rays 140. A focusing optic could be beneficial when x-ray source 100 is to be employed in connection with an x-ray fluorescence system, while still requiring a low power source. As an alternative, optic 135 could comprise a collimating optical element for use in applications which require a parallel beam of x-ray radiation output from the optic (not shown). In the case of a collimating optical element, x-rays 140 would be parallel rather than converging to spot 145 as shown in FIG. 1.

Optic 135 could comprise any optical element capable of manipulating x-rays, for example, for focusing or collimating. By way of example, optic 135 could comprise a polycapillary bundle (such as available from X-ray Optical Systems, Inc. of Albany, N.Y.), a doubly curved crystal or other optical element form. (A polycapillary optic is a bundle of thin, hollow tubes that transmit photons via total reflection. Such an optic is described, for example, in U.S. Pat. Nos. 5,175,755, 5,192,869, and 5,497,008.) Upon calibration of x-ray source assembly 100, optic 135 remains stationary (in one embodiment) relative to x-ray source 101 until further calibration of x-ray source assembly 100 is performed.

The end of HV anode 125 opposite the impingement surface protrudes through the body of x-ray tube 105 and is mechanically and electrically connected to a base assembly 150. Base assembly 150 includes a first conductor disc 155 that is electrically isolated from a base plate 165 via a dielectric disc 160. The resulting anode 125 and base assembly 150 structure, also referred to herein as the anode stack, is described in detail in the above-incorporated patent application entitled "Method and Device For Cooling and Electrically Insulating A High-Voltage, Heat Generating Component".

FIG. 1 also shows a schematic associated with electron gun 115 having a filament 116 and the different current applied thereto. The delivery of current for heating up filament 116 occurs by a high-voltage lead connected to filament 116. Filament 116 of electron gun 115 includes current y passing therethrough from the high-voltage lead. Current x is supplied from ground which is tied to one terminal of filament 116. Current z is supplied from ground which is coupled to electron gun 115.

During operation, heat generated in the filament of electron gun 115 causes the filament to shrink or evaporate (e.g., evaporation of tungsten atoms from a tungsten filament). As a result of this shrinkage, the diameter as well as the surface area of the filament decreases. As the diameter and surface area decrease, the resistance of the filament increases. In order for the filament to emit the same number of electrons to keep the beam current the same at this reduced surface area, the filament increases in temperature. As a result of this increased temperature and shrinkage in diameter, the filament will gradually degrade and eventually fail. Currently, the degradation of the filament is not monitored and there is no anticipation of its failure.

In accordance with an aspect of the present invention, a diagnostic system is implemented within x-ray source assembly 100. This diagnostic system within x-ray source assembly comprises the ability to monitor or detect the existing operating conditions of certain components within the x-ray source. This diagnostic system also comprises storage capability to maintain a record of reference operating conditions (e.g., initial test results, prior operations), which, in one example, may be predetermined based on past performance of the same or similar component. This enables the diagnostic system to keep a history of operation for future evaluation and comparison to, for example, track component degradation during the life of the x-ray source and anticipate failure. This diagnostic system also comprises processing capability to evaluate existing operating conditions with the reference or predetermined operating conditions stored in memory. The history information can be used to calculate the rates of change of any of the sensed operating conditions over any desired time period.

In one aspect, diagnostic system includes, for example, a processor 160, which is shown embedded within housing 110, as well as one or more sensors associated with one or more components of the x-ray source assembly 100. The diagnostic system has an input circuit which receives output signals provided from the sensors (e.g. 162) associated with certain components of the x-ray source assembly. Processor 160 reads those input signals applied to the input circuit and executes data processing operations, according to programs and constants stored in, for example, Read-Only Memory. Processor 160 may be a general purpose programed microprocessor or, alternatively, non-volatile, writeable memory such as, for example, a flash-memory semiconductor. By way of example, the processor might comprise a Motorola HC12 processor. Processor 160 may include at least one storage device, and data interpolation and comparison capabilities.

Sensors may be employed to measure existing operating conditions such as, for example, temperature within the x-ray source, pressure within the vacuum, the different currents passing through the filament of electron gun 115, and power or voltage supplied by the power supply, as well as other detectable operating conditions of the x-ray source assembly. In one example, a sensor 162 includes an amperage sensor physically coupled to electron gun 115. This amperage sensor 162 could comprise, for example, any means for detecting the current passing through the filament of electron gun 115 from the power supply or a ground location. By way of example, the amperage sensor might comprise a current shunt resistor.

In accordance with one aspect of the present invention, the diagnostic system may passively store information concerning the history of operating conditions and the identity of the x-ray source assembly 100 such as, for example, manufacturing information, warranty data, life expectancy, initial test results, and actual operation time or stamped time. This stored information could provide a manufacturer with a history or record of operation to assist in future construction and improvements of x-ray source assemblies or assist a manufacturer identify and determine why the particular x-ray source failed.

In accordance with another aspect of the present invention, the diagnostic system may actively communicate with an operator or network 170 (e.g. outside source) to warn against the failure of the components monitored by the diagnostic system. In one embodiment, the diagnostic system may communicate with certain components of the x-ray source assembly to control the operation of such components based on existing or desired operating conditions of other components. In another embodiment, the diagnostic system may directly control components outside the x-ray source such as, for example, to shut off something, e.g. voltage, because the monitored component is about to fail.

Figure 2:
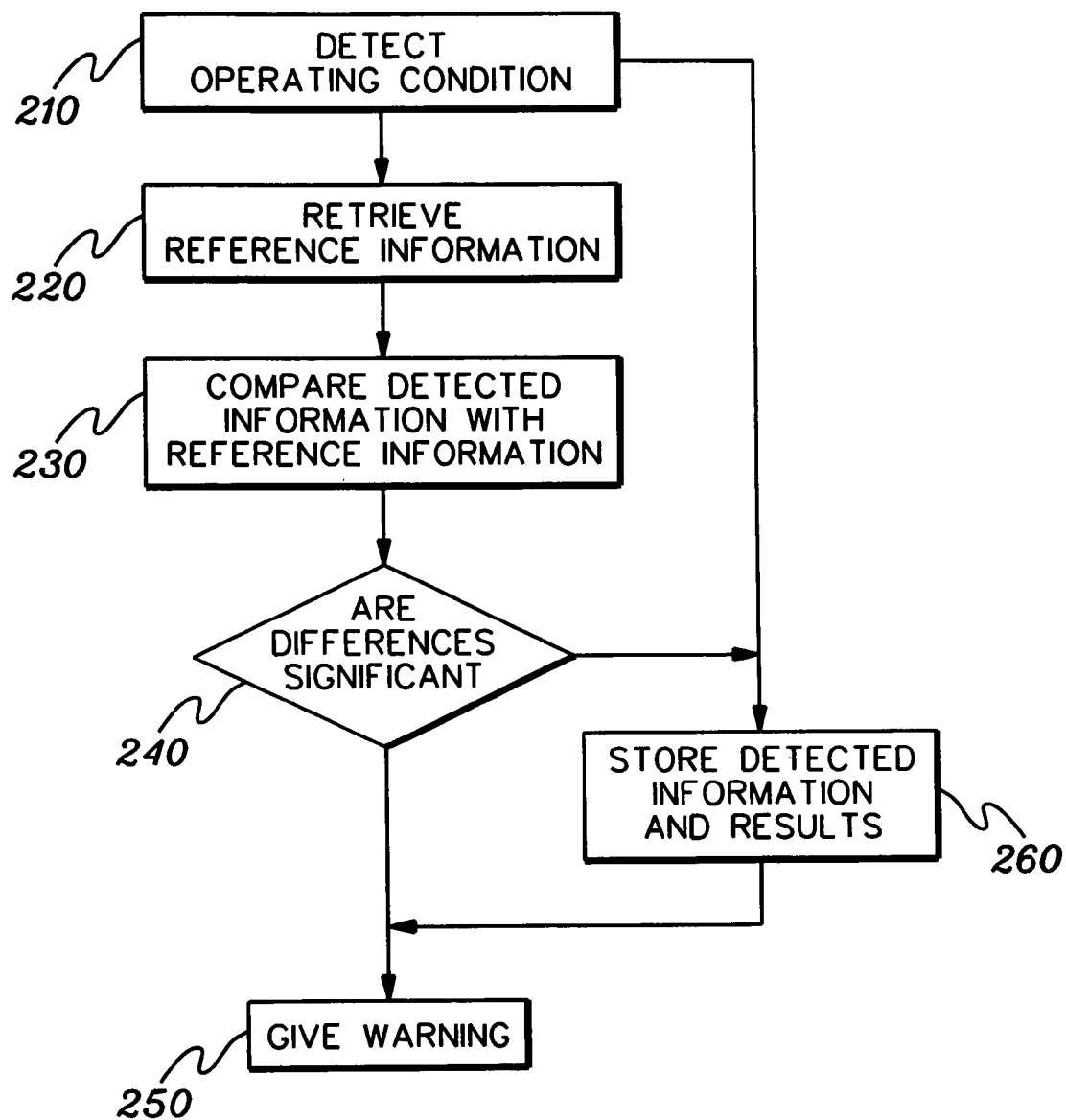
FIG. 2 is a representation of one embodiment of processing implemented by the processor of the diagnostic system of an x-ray source assembly in accordance with an aspect of the present invention.

FIG. 2 is a flowchart of one embodiment of processing 200 which may be implemented by processor of FIG. 1. As shown in FIG. 2, processing 200 begins by detecting or measuring 210 the existing operating conditions of one or more components of x-ray source assembly 100. In one embodiment, current y from the power supply or current y and voltage passing through filament 116 of electron gun 115 is measured. As noted above, current y passing through filament 116 of the electron gun can be obtained from the filament using a sensor 162 physically attached to filament 116, with the resultant signal fed back to the processor 160 embedded within housing 110 of x-ray source assembly 100. In another embodiment, processor 160 receives signals including other characteristics of the x-ray source, such as, for example, the voltage supplied by the power supply which supplies power to electron gun 115, the amperage being drawn by the power supply, the pressure or temperature within the x-ray tube and the like. Processor 160 may also receive signals including other characteristics such as, for example, the spectral output of x-rays, condition of any cooling system utilized, and the spot size and position.

Processor 160 of the diagnostic system will then look up or retrieve reference information 220 concerning the past performance or desired operating conditions of the monitored component(s). Reference information is read out or retrieved from, for example, memory cells. In an embodiment that monitors the amount of current y or current y and voltage passing through filament 116 in electron gun 115, the reference current could be a predetermined current for the filament at a measured power level. This reference current could be determined during a calibration or test procedure or based on warranty information or derived from a previous evaluation of the component for the x-ray source assembly as derived from a look-up table and stored in memory, and may be unique to a particular assembly or generic to a plurality of identically manufactured x-ray source assemblies.

Once the reference condition is obtained, processor 160 will compare the detected or measured operating condition of the component with the reference operating condition retrieved from memory 230. For example, the reference current and the read current are fed to a comparison algorithm. The algorithm is employed to calculate the difference in performance of the component. One of ordinary skill in the art can readily implement an algorithm to accomplish this function. Alternatively, since the same voltage is applied across the filament and current is obtained from a sensor 162, the resistance of the filament can be determined by a well known algorithm. Based on the determined resistance, the diagnostic system could be programmed to recognize critical resistance values in the filament and progress the operation and degradation of the filament.

A query 240 is then made to determine whether or not the differences between the read data and the reference data have reached a predetermined or flagged value to warrant signaling of a warning to a user or maintenance personnel. In one embodiment, processor 160 decides whether or not the certain component is malfunctioning or degrading to the point of failure on the comparison between the detected operating condition and the reference operating condition retrieved from storage. If the existing operating condition as compared to the reference operating condition is significant enough based on expected or satisfactory conditions as stored in the processor, processor 160 will provide a warning of a failure or potential for a failure of the certain component as indicated by block 250. Alternatively, processor 160 may look at trend data from, for example, a control plot. In other words, the criteria for failure may be based on a trend, e.g. stable or unstable, instead of a value to value comparison.

Processor 160 analyzes the signals transmitted to it, and may provide output in a user-friendly format such as through an indicator light, or other visual display, or alternatively, through other indications such as audible signals, to notify or warn the user or maintenance personnel of the condition of the x-ray source assembly. It will be apparent to those skilled in the art that other modes of output may also be advantageously employed to accomplish the same purpose.

After processing and warning, if applicable, processor 160 stores 260 the detected operating conditions and the results of any comparisons, calculations and warnings in memory for future use and evaluation of the performance history of the x-ray source assembly 100. When a comparison is made or a warning is given, it is preferable to store information about the comparisons or warnings in a data storage device and to inform an operator or manufacturer by a warning device (e.g., indicator light or audible signal). In one example, the stored information may be used to make a performance graph or may be compared to the performance or operation of other x-ray source assemblies.

It is recognized that processor 160 may execute different programs from those discussed above to detect a malfunction of other components of the x-ray source assembly 100. A greater number of sensing elements could be provided if desired for more complete and accurate sampling of the operating conditions of the x-ray source assembly 100, but are not necessary for adequate implementation of the present invention.

Figure 3:
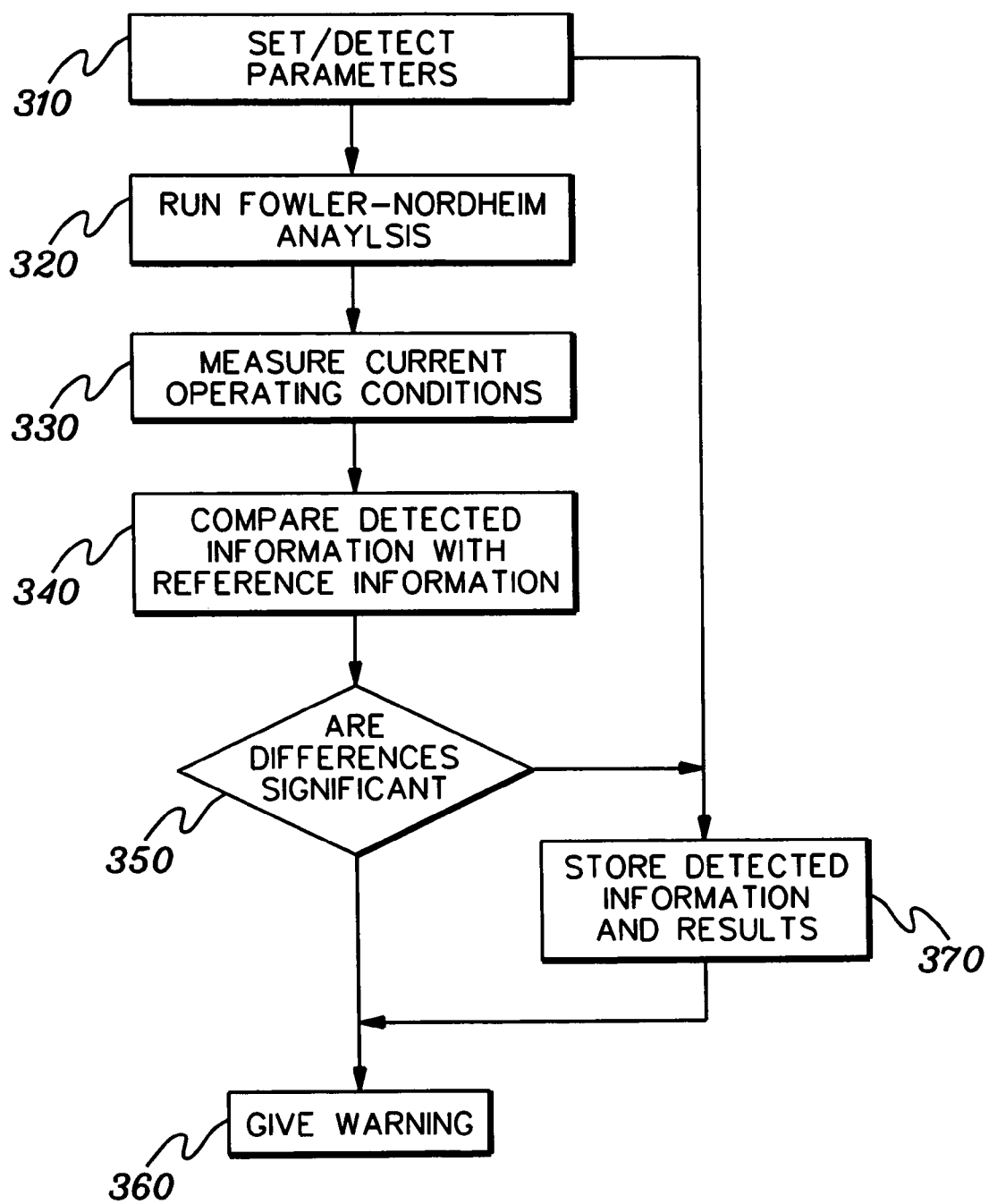
FIG. 3 is a representation of another embodiment of processing implemented by the processor of the diagnostic system of an x-ray source assembly in accordance with an aspect of the present invention.

FIG. 3 is a flowchart of another embodiment of processing 300 which may be implemented by processor of FIG. 1 to derive at a Fowler-Nordheim plot. A Fowler-Nordheim model for field emission describes the electron current density emitting from a surface into vacuum as a function of applied electric field during non-normal conditions (e.g., when the filament is cold). The model parameters which govern the emission are the material (effective work function), the area available for emission and a geometric enhancement factor. The enhancement factor describes how electric fields can be enhanced by protrusions from the emitting surface. The information concerning conducting a Fowler-Nordheim analysis, including relevant algorithms, are well known in the art.

In the case of x-ray source assembly 100, by measuring the current flowing from the surface of electron gun 115 when the filament is cold (e.g. current x or currents x and z), Fowler-Nordheim will provide the sharpness of protrusions on the surface and the area of these protrusions. Current x or current x and z may be measured by, for example, a nano-amperage meter. From this, changes in the characteristics or changes in performance can be determined to warn of failure or track degradation of the x-ray tube. The failure criterion may be preselected from the Fowler-Nordheim breakdown curves generated by the x-ray tube under test and stored in memory by known methods.

As shown in FIG. 3, processing 300 begins by setting the parameters 310 (e.g. voltage, temperature) for the x-ray source for creation of a Fowler-Nordheim plot. In this embodiment, processor 160 may communicate with the x-ray source assembly 100 to run a Fowler-Nordheim analysis by, for example, running or controlling the power supply at a certain level during non-normal (e.g. cold filament) operating conditions. Alternatively, the diagnostic system may be pre-programed to recognize, and wait for, the desired parameters for a Fowler-Nordheim analysis by comparing stored, desired parameters with existing operating conditions until such desired parameters exist. Once the desired parameters exist, the diagnostic system will run a Fowler-Nordheim analysis 320.

While the parameters for the Fowler-Nordheim analysis are run, the existing operating conditions are measured or detected 330 and compared 340 to reference operating conditions stored in memory. Similar to the previous example, a query 350 is then made to determine whether the comparison results require warning 360 to, for example, a network or maintenance personnel. After processing, processor 160 stores 370 the detected operating conditions and the results of any comparisons, calculations and warnings in memory for future use and evaluation of the performance or operation history of the x-ray source assembly.

In another aspect of the present invention, processor 160 may be employed to communicate with other components outside the x-ray tube such as, for example, an optics system monitoring and/or controlling the optics for the x-ray source assembly, a power supply, a sample positioning system that monitors and controls the source to be x-rayed by the x-ray source assembly or a network (e.g. Internet). For example, the other components of the x-ray source assembly 100 may have its own processor for controlling functions and monitoring operation of the certain components. In an alternate embodiment, one processor may be employed to monitor and control multiple components of the x-ray source assembly and communicate with a network or outside source (e.g. internet, central computer).

Figure 4:
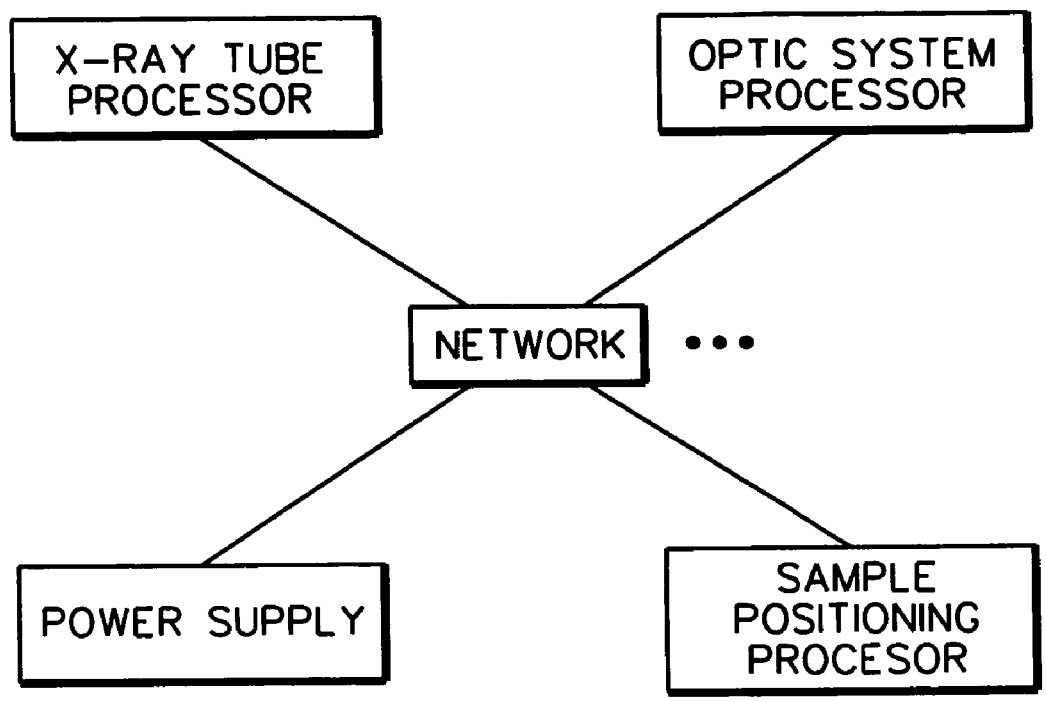
FIG. 4 is a block diagram of one embodiment of a diagnosing system for an x-ray source assembly, in accordance with an aspect of the present invention.

By using a plurality of processors, or alternatively one processor, to monitor and control separate components and communicate with the other components of the x-ray source assembly, the entire x-ray source assembly may be configured to calibrate or re-calibrate itself over time or operate in response to information from a network or operator, or associated with operating conditions of one of the components. Each of these processors may be configured to communicate with each other directly or, alternatively through a network, as shown in FIG. 4, with operator interface capability by, for example, program codes and commands recognized by all of the processors.

In an embodiment using multiple processors, the processors may be coupled directly to the other processors or by, for example, a network, a central computer or other means enabling communication. Each of these processors, or alternatively a central processor controlling all of the components, may also be programmed or capable of identifying or recognizing the other components when attached to the system and receiving information associated with the other processors or components from other processors and sensors.

In one aspect of the present invention, there is an optic system controlling the type and positioning of the optic depending on, for example, the desired location from the transmission window 107 or type of x-ray desired. As one example, a central processor or operator through a network may instruct the optic system to automatically change the optic type depending on the desired x-ray function as well as communicate with the power supply to change the voltage and amperage supplied to the x-ray source, or with a sample positioning system to control the location of the sample to be x-rayed based on a change in the focal point of the new optic.

In another aspect of the present invention, the x-ray source may communicate or drive or control other parts of the x-ray source assembly. In one embodiment, a program in an analyzer tells the source to wait to do a predetermined analysis. The source then directs, for example, the positioning of the sample, the optic, the power level, how to set up detectors or sensors and the like. If the x-ray source is changed or replaced, the new x-ray source may be program to conduct the analysis differently based on what it knows about itself. In one embodiment, a USB device may be added to give information to, e.g., the system software.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A diagnosing system for a x-ray source assembly comprising:
    a monitoring element configured to detect at least one existing operating condition of at least one component of the x-ray source assembly; and
    a processing element configured to compare the at least one existing operating condition detected by said monitoring element with at least one reference operating condition generated using a Fowler-Nordheim model for field emission current as a function of applied electric field, to determine a characteristic of the at least one component.

2. The diagnosing system of claim 1, wherein said processing element determines aging of the at least one component of the x-ray source assembly from the comparison of the at least one existing operating condition with the at least one reference operating condition.

3. The diagnosing system of claim 1, wherein said processing element anticipates failure of the at least one component of the x-ray source assembly based on the comparison of the at least one existing operating condition with the at least one reference operating condition.

4. The diagnosing system of claim 1, wherein said processing element is further configured to store the detected existing operating conditions and results from comparisons of the detected existing operating conditions with the reference operating conditions.

5. The diagnosing system of claim 1, wherein said processing element provides an indication that an existing operating condition of the monitored component is operating at a predetermined condition as compared to a reference operating condition.

6. The diagnosing system of claim 1, wherein said monitoring element comprises at least one sensor coupled to a component of the x-ray source assembly to detect the existing operating condition of the component.

7. The diagnosing system of claim 6, wherein the at least one sensor is coupled to an electron gun of the x-ray source assembly.

8. The diagnosing system of claim 7, wherein the at least one sensor coupled to the electron gun detects current passing through a filament of the electron gun.

9. The diagnosing system of claim 8, wherein the processing element anticipates failure of the filament of the electron gun based on a comparison of existing current passing through the filament and a reference current passing through the filament.

10. The diagnosing system of claim 9, wherein the processing element anticipates failure by sending a warning to an operator.

11. The diagnosing system of claim 1, wherein the at least one sensor is configured to provide feedback related to current passing through the electron gun.

12. The diagnosing system of claim 1, wherein, for a given power source, said processing element is configured to control the operation of at least one component of the x-ray source assembly based on existing operating conditions detected by the monitoring element.

13. The diagnosing system of claim 8, wherein, for a given power source, the processing element anticipates failure of the filament of the electron gun based on a comparison of existing resistance of the filament and a reference resistance of the filament.

14. A diagnosing system for a x-ray source assembly, said diagnosing system comprising:
    a first processing element configured to monitor existing operating conditions of a first component of the x-ray source assembly;
    means for comparing the existing operating conditions with at least one reference operating condition generated using a Fowler-Nordheim model for field emission current as a function of applied electric field; and
    a second processing element associated with a second component of the x-ray source assembly and coupled to said first processing element, said second processing element configured to receive information associated with existing operating conditions from the first processing element.

15. The diagnosing system of claim 14, wherein said second processing element controls the second component of the x-ray source assembly based on the information received from the first processing element associated with existing operating conditions from the first processing element.

16. The diagnosing system of claim 15, wherein said first processing element communicates with said second processing element using a network.

17. A method for diagnosing an x-ray source assembly comprising:
    detecting at least one existing operating condition of at least one component of the x-ray source assembly; and
    comparing the at least one existing operating condition with at least one reference operating condition generated using a Fowler-Nordheim model for field emission current as a function of applied electric field, to determine a characteristic of the at least one component.

18. The method of claim 17, further comprising:
    determining aging of the at least one component of the x-ray source assembly from the comparison of the at least one existing operating condition with the at least one reference operating condition.

19. The method of claim 17, further comprising:
    anticipating failure of the at least one component of the x-ray source assembly based on the comparison of the at least one existing operating condition with the at least one reference operating condition.

20. The method of claim 17, further comprising:
    providing an indication that an existing operating condition of the monitored component is operating at a predetermined condition as compared to a reference operating condition.

21. The method of claim 17, further comprising:
    anticipating failure of a filament of an electron gun of the x-ray source assembly based on a comparison of existing current passing through the filament and a reference current passing through the filament.

* * * * *